United States Patent
Feliers et al.

(10) Patent No.: US 8,449,766 B2
(45) Date of Patent: May 28, 2013

(54) DEVICE FOR CAPTURING ODOR AND/OR TASTE-GENERATING SUBSTANCES PRESENT IN WATER FLOWING IN A NETWORK

(75) Inventors: Cédric Feliers, Eragny sur Oise (FR); Elise Corbi, Saint Germain en Laye (FR); David Benanou, Sartrouville (FR)

(73) Assignee: Veolia Eau, Compagnie Generale des Eaux, Paris (FR)

(*) Notice: Subject to any disclaimer, the term of this patent is extended or adjusted under 35 U.S.C. 154(b) by 416 days.

(21) Appl. No.: 12/373,305

(22) PCT Filed: Jul. 12, 2007

(86) PCT No.: PCT/FR2007/051655
§ 371 (c)(1),
(2), (4) Date: Jun. 5, 2009

(87) PCT Pub. No.: WO2008/007032
PCT Pub. Date: Jan. 17, 2008

(65) Prior Publication Data
US 2009/0289010 A1  Nov. 26, 2009

(30) Foreign Application Priority Data
Jul. 13, 2006 (FR) ..................... 06 52957

(51) Int. Cl.
*G01N 1/20* (2006.01)
(52) U.S. Cl.
USPC .......... 210/93; 210/322; 210/449; 210/502.1; 422/69
(58) Field of Classification Search
USPC .......... 210/93, 322, 449, 502.1, 662; 422/69, 422/70
See application file for complete search history.

(56) References Cited

U.S. PATENT DOCUMENTS

| | | | |
|---|---|---|---|
| 2,752,309 A * | 6/1956 | Emmons et al. | 210/668 |
| 3,327,859 A * | 6/1967 | Pall | 210/266 |
| 3,628,915 A * | 12/1971 | Robertson | 436/165 |
| 3,655,052 A * | 4/1972 | Friederichs et al. | 210/90 |
| 3,822,018 A * | 7/1974 | Krongos | 210/323.2 |
| 4,668,386 A * | 5/1987 | Seal et al. | 210/91 |
| 5,256,287 A | 10/1993 | Underwood | |
| 5,653,875 A * | 8/1997 | Betz et al. | 210/198.2 |
| 5,868,933 A | 2/1999 | Patrick et al. | |

(Continued)

FOREIGN PATENT DOCUMENTS

| | | |
|---|---|---|
| FR | 2 407 730 | 6/1979 |
| FR | 2 760 837 | 9/1998 |
| WO | WO 93/24203 | 12/1993 |
| WO | WO 9706888 A1 * | 2/1997 |

OTHER PUBLICATIONS

The Search Report corresponding to the PCT/FR2007/051655 application.

(Continued)

*Primary Examiner* — Matthew O Savage
(74) *Attorney, Agent, or Firm* — Kilpatrick Townsend & Stockton LLP

(57) ABSTRACT

The invention relates to a device (10) for capturing odor- and/or taste-generating substances present in water flowing continuously in a water distribution network via a pipe (12). In characteristic manner, the device comprises:
- capture means (22) for capturing said substances;
- at least one chamber (18) containing said capture means (22) and suitable for having network water flow therethrough; and
- hydraulic link and connection means (14; 42) between said chamber (18) and said pipe (12).

The invention is applicable to networks for distributing drinking water.

4 Claims, 4 Drawing Sheets

U.S. PATENT DOCUMENTS

2006/0219636 A1* 10/2006 Plumb et al. .................. 210/656

OTHER PUBLICATIONS

Baltussen, et al., "Stir Bar Sorptive Extraction (SBSE), a Novel Extraction Technique for Aqueous Samples Theory and Principles", J. Microcolumn Separations, 1999, 4 pages.

Baltussen, et al., "Sorptive Sample Preparation—a Review", Anal Bioanal Chem, 2002, 7 pages.

Kawaguchi, et al., "Novel Stir Bar Sorptive Extraction Methods for Environmental and Biomedical Analysis", Journal of Pharmaceutical and Biomedical Analysis, 2006, 4 pages.

* cited by examiner

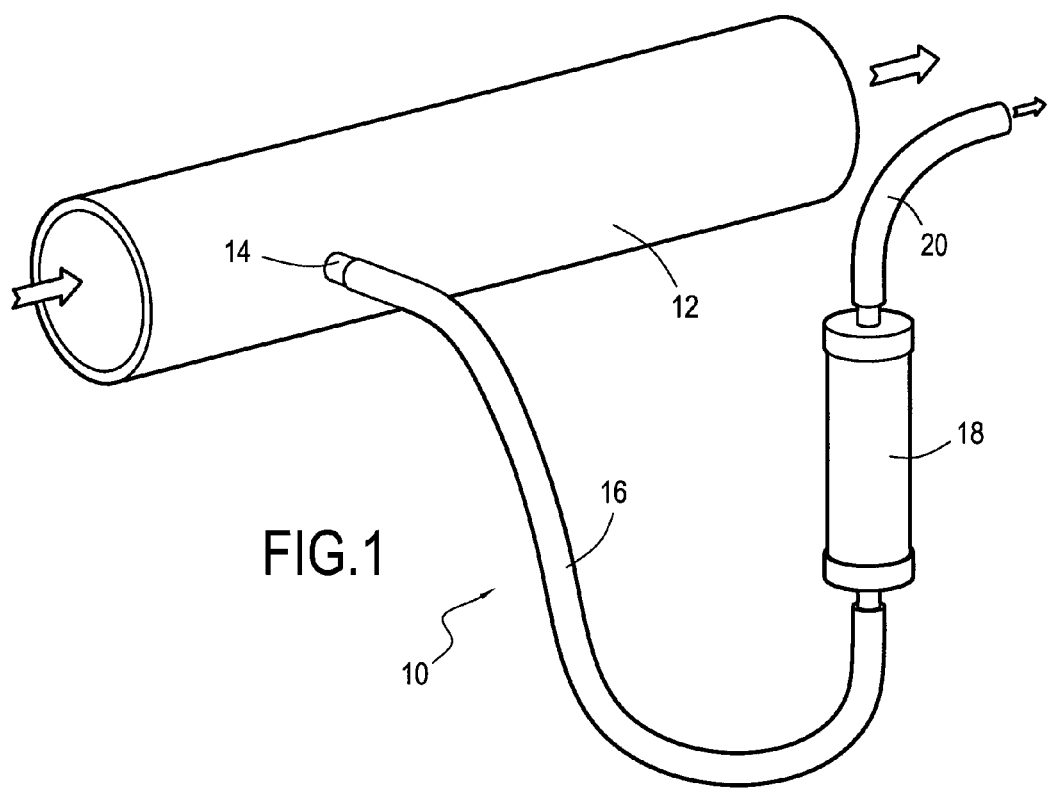
FIG.1
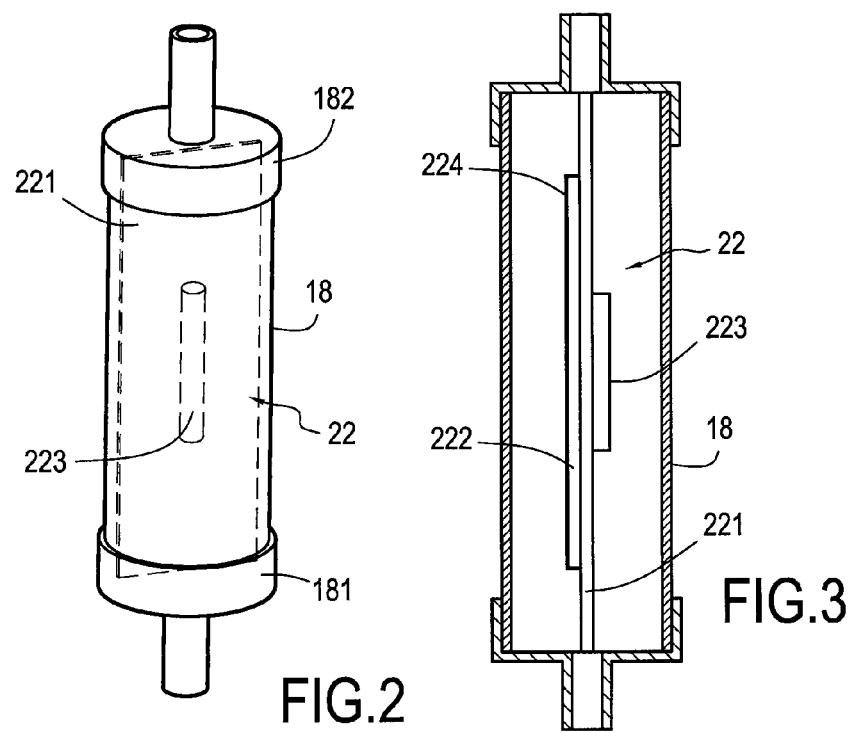
FIG.2
FIG.3

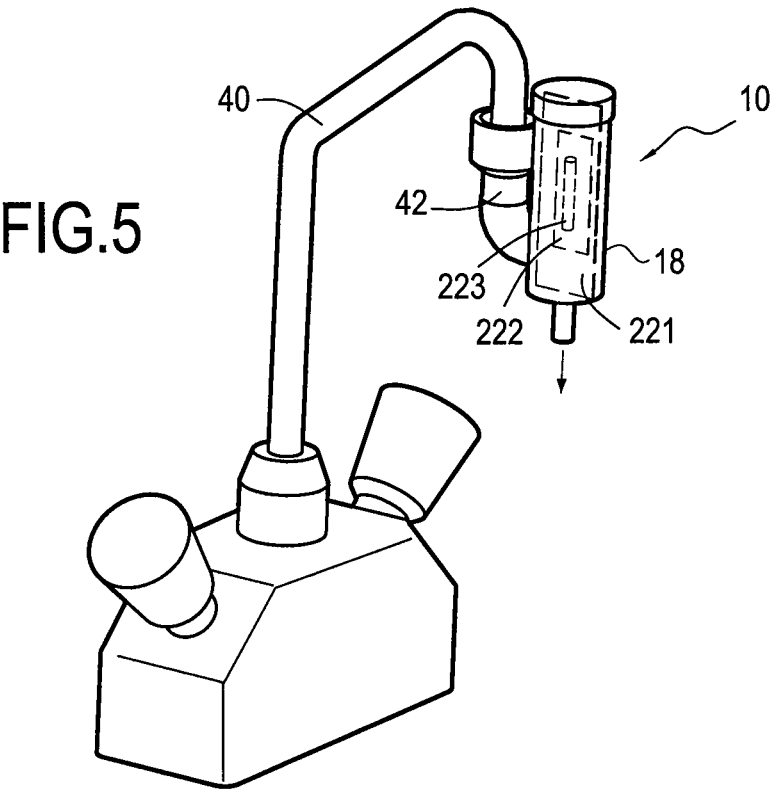
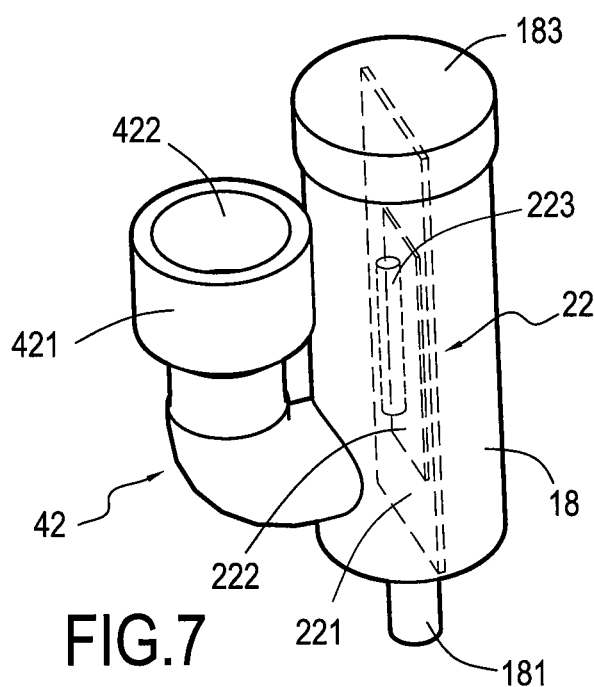
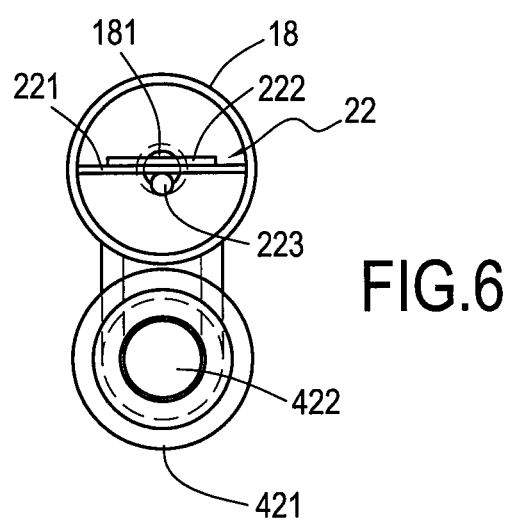

DEVICE FOR CAPTURING ODOR AND/OR TASTE-GENERATING SUBSTANCES PRESENT IN WATER FLOWING IN A NETWORK

FIELD OF THE INVENTION

The invention relates to water distribution networks, and in particular to networks for distributing drinking water. More precisely, the invention relates to a device and a method for capturing odor- and/or taste-generating substances present in the water flowing in a pipe of a water distribution network.

BACKGROUND

The term "capture" is used to mean trapping or extracting odor- and/or taste-generating substances in order to characterize them, as opposed to systematically eliminating them.

In this field, there is a legal requirement to monitor water quality, either periodically or as a function of needs, and very particularly to monitor drinking water distributed by a network.

Such inspections can be triggered in particular when a possibly characteristic taste and/or odor is detected by a customer or a user of the distribution network.

At present, when a bad taste and/or a bad odor is detected in water, the procedure is as follows:
the person concerned calls the complaints center associated with the water distribution network;
a member of the water distribution network staff goes to the premises where the detection occurred in order to bottle a sample of water;
the sample is then sent to an analysis laboratory;
substances generating the taste and/or odors in question are then extracted; and
the extracted substances are analyzed.

Concerning the above steps, it is considered that extraction requires a duration of about two hours while an analysis can be performed within the following 24 hours.

Nevertheless, it is known for taste- and/or odor-generating substances to appear in water intermittently over time and that the odor (or taste) thresholds of the compounds in question are extremely low compared with the sensitivity of commonly-used detection equipment.

Consequently, the above-described procedure very rapidly reaches its limits in terms of effectiveness.

In other words, that prior art procedure raises the problem of conserving the entire "matrix" responsible for the taste and the odor of the water, between the time a sample is taken and the time extraction is performed in the laboratory, and the time lapse between the taster detecting the taste and the time a sample is taken is also often too long.

Nevertheless, that is a procedure that is normally used for characterizing the origin of the odor or the taste of certain waters.

SUMMARY

An object of the present invention is to provide a device and a method enabling the drawbacks of the prior art to be overcome, and in particular making it possible to extract the compounds that might correspond to taste- and/or odor-generating substances directly from the water network.

In particular, it is desired to provide a device and a method that make it possible, at least at the selected moment, and continuously, to extract the intermittently-present molecules that might correspond to the taste- and/or odor-generating substances, which device and method present simplicity and speed of implementation, and also greater sensitivity, by accumulating odor molecules from the sample over time.

To this end, according to the present invention, the device for capturing odor- and/or taste-generating substances present in water flowing continuously in a water distribution network via a pipe is characterized in that it comprises:
capture means for capturing said substances, said capture means being of the type acting by sorption;
at least one chamber containing said capture means and suitable for having network water flow therethrough; and
hydraulic link and connection means between said chamber and said pipe.

In this way, it can be understood that by positioning the device it is possible to capture on a continuous basis from the network any odor- and/or taste-generating substances present in the water at any moment, and in particular regularly for the purpose of monitoring water quality without involving personnel in the extraction step, thereby limiting the corresponding costs.

This solution also presents the additional advantage of making it possible not only to extract water easily in situ, but also to do so over a long period, thereby enabling molecules that are responsible for the taste and/or odor of the water to be captured even when they appear intermittently.

For example, the chamber providing contact between the water and the capture means is formed by a tube that is open at both ends.

Overall, the solution of the present invention makes it possible significantly to improve performance in searching for odorous compounds in order to identify the looked-for substances, and consequently to take early action seeking to improve water quality.

Said capture means of the type acting by sorption preferably comprise at least one support receiving at least one capture element comprising a layer of polydimethylsiloxane (PDMS) (where PDMS is capable of directly covering the support or else can be situated on the surface of the capture element that is itself mounted on the support).

Likewise preferably, said support includes a magnetic portion, the magnetic portion being covered by a polymer of the polydimethylsiloxane (PDMS) type. For example, the magnetic portion may be a glass bar covered in a polymer of the polydimethylsiloxane (PDMS) type, and having a magnetic bar encapsulated therein.

Capture means of this type are described in patents EP 1 039 288, EP 1 406 077, and EP 1 610 124 in the name of the company Gerstel Systemtechnik GmbH & Co., KG.

According to the invention, in order to avoid making subsequent measurements erroneous as a result of the materials used in the device and that come into contact with the water, provision is advantageously made for the materials constituting the device not to give off compounds that might impede the capture of odorous molecules. For example, use is made of polytetrafluoroethylene (PTFE) or Teflon (registered trademark), of stainless steel, and/or of glass.

Furthermore, in a preferred embodiment, said hydraulic link and connection means comprise a quick-coupling system for coupling to an outlet faucet on user premises.

In another preferred embodiment, said hydraulic link and connection means comprise tapping means (i.e. means for making a wet connection) between the pipe and said chamber, together with means for discharging water from said chamber. Thus, a water connection is made without interrupting the flow along the distribution pipe for a city or a building. By way of example, the tapping comprises a coupling constituted essentially by a pipe saddle and a stop cock.

Provision can also be made for said tapping means to include a stop cock or valve.

Advantageously, it is also possible to provide for said tapping means to include a releasable fastener system enabling the chamber to be replaced easily.

In another advantageous disposition, said hydraulic link and connection means includes a flowmeter. Where appropriate, the flowmeter makes it possible to control the flow rate of water through the contact chamber.

In a variant embodiment, the device further includes a system enabling a liquid solution acting as a standard to be injected into said chamber together with the water flowing therethrough. The liquid solution is a solution containing one or more identified standard molecules suitable for being absorbed by the sorption support, and enabling trapped compounds to be quantified.

The present invention also provides a method of capturing odor- and/or taste-generating substances present in water flowing continuously in a water distribution network via a pipe.

To this end, the invention provides for the capture method to be implemented by passing network water through a chamber containing capture means for capturing said substances and connected to the pipe via hydraulic link and connection means.

One or more of the following dispositions is/are preferably adopted:
the flow of water through the chamber is also measured and/or adjusted; and
a liquid solution acting as a standard is also injected into said chamber at the same time as water flows therethrough.

In the context of the present invention, the method described is implemented and the device described is used in particular for a drinking water network.

BRIEF DESCRIPTION OF THE DRAWINGS

Other advantages and characteristics of the invention appear on reading the following description made by way of example and with reference to the accompanying drawings, in which:

FIG. 1 is a diagrammatic overall perspective view of the device of the invention;

FIG. 2 shows in greater detail the chamber and the means for capturing odor- and/or taste-generating substances present in water;

FIG. 3 is a profile view of the capture means contained in the chamber shown in FIG. 2;

FIGS. 5 to 7 show another variant embodiment of the device in accordance with the invention.

DETAILED DESCRIPTION

Figure 4:
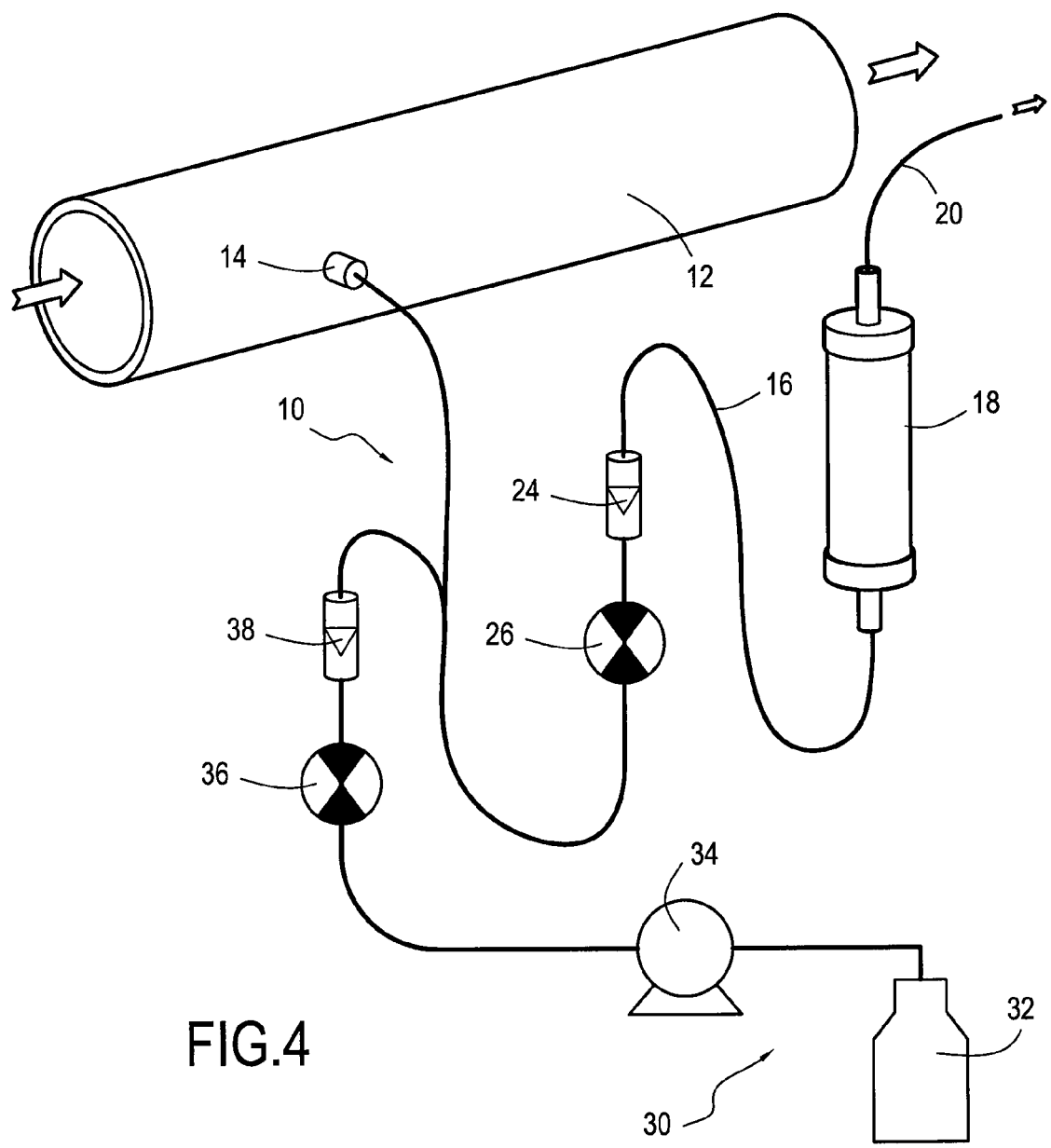
FIG. 4 is a diagrammatic overall perspective view of a variant of the device of the invention.

In FIG. 1, there can be seen a device 10 in accordance with the present invention that is mounted on a mains pipe 12, e.g. forming part of a drinking water distribution network. To this end, tapping means 14 is mounted on the pipe 12 and is connected via a first hose 16 to the inlet of a chamber 18 whose outlet is connected to a second hose for delivering water.

The tapping means 14 and the first hose 16 form hydraulic linking and connection means between the chamber 18 and the mains pipe 12. It should be observed that the tapping means 14, generally constituted by a pipe saddle and a stop cock, may form a releasable fastener system for mounting the first hose 16 and thus the chamber 18 on the pipe 12.

As can be seen more clearly in FIG. 2, the chamber 18 is a tube of cylindrical section, preferably made of stainless steel or of polytetrafluoroethylene (PTFE), that is closed at both ends by respective leaktight couplings 181 and 182 enabling the space contained within the chamber 18 to be connected respectively to the first hose 16 and to the second hose 20.

In addition, the chamber 18 contains capture means 22 for capturing odor- and/or taste-generating substances present in the water flowing in the pipe 12. For this purpose, in the embodiment shown (see FIGS. 2, 3, 6, and 7), this capture means 22 comprises a support plate 221 having mounted on the back thereof a magnetic plate 222 that serves to hold the capture element 223 that acts by sorption of odor- and/or taste-generating substances by a magnetic effect, the capture element 223 being mounted on the other side of the support plate 221.

The support plate 221 is preferably made of stainless steel and the magnetic plate 222 is covered in a layer 224 of Teflon or PTFE.

All of the materials of the chamber 18 and of the capture means 22 are selected to avoid releasing any substance that might hinder the capture of molecules responsible for taste and/or odors in water: specifically use is made of stainless steel, of glass, and/or of Teflon (registered trademark).

The magnetic plate 222 is preferably stapled to the support plate 221 and serves essentially to retain the sorption support 223 that includes the layer of polydimethylsiloxane (PDMS).

In the example shown, the capture element 223 acting by sorption is a traditional magnetic bar that is commercially available, comprising an elongate magnet coated in a sheath of glass and having a sleeve of polydimethylsiloxane (PDMS) mounted around the sheath of glass to form the sorption element proper.

As an alternative (not shown), the capture element 223 can be formed of a layer of polydimethylsiloxane (PDMS) connected by adhesive means to the support plate 221 like a patch (under such circumstances there is no need for the magnetic plate 221 nor for its layer 224 of PTFE, if any).

It can thus be understood that by passing water coming from the pipe 12 through the chamber 18, substances that might be those responsible for the taste and/or odors of the water can be captured continuously by the capture means 22. Such capture is performed so long as water flows through the chamber 18 going from the pipe 12 via the first hose 16 and then out from the chamber 18 prior to being discharge via the discharge second hose 20 to a drain.

It should be understood that the chamber 18 forms a contact chamber that may include a plurality of capture elements 223 acting by sorption that may be arranged in series or in parallel.

Likewise, it is possible to provide a plurality of chambers 18 in series or in parallel downstream from the tapping means 14 mounted on the pipe 12.

After sufficient exposure to water coming from the distribution network via the pipe and the tapping means 14, where this period is defined by the user, and/or possibly together with information documentation, the capture means 22 is extracted from the chamber 18 by opening at least one of the two couplings 181 and 182, and then the capture element 223 acting by sorption is used for performing an analysis in order to detect the molecules responsible for the tastes and the odors of the water.

In the variant embodiment shown in FIG. 4, between the tapping means 14 and the chamber 18, the first hose 16 is fitted with a flowmeter 24 and a gate valve 26, in order to measure the rate at which water flows towards the chamber 18, while also enabling this rate to be adjusted.

Furthermore, in FIG. 4, there is provided a system 30 for injecting a standard solution in parallel into the chamber 18, the standard solution containing a known concentration of at least one well-identified molecule capable of being absorbed by the capture elements 223 acting by sorption. The standard solution is contained in a bottle 32, itself connected to the first hose 16 via a pump 34 and possibly via a gate valve 26 associated with another flowmeter 38.

Thus, in this configuration, the capture device 10 is fed with the standard solution contained in the bottle 32 by the pump 34 operating at a constant rate and adjusted as a function of the feed rate measured by the flowmeter 24 situated upstream from the chamber 18, and also as a function of the concentration of the standard solution.

In another alternative embodiment, shown in FIGS. 5 to 7, it is possible to fasten the device 10 directly to the end of a faucet 40. Under such circumstances, and as can be seen more clearly in FIGS. 6 and 7, instead of using the tapping means 14 and the first hose 16 to provide the hydraulic link and connection means between the chamber 18 and one end of the faucet 40, a quick-coupling system 42 is used.

The quick-coupling system 42 as shown in FIGS. 5 and 7 is constituted by an endpiece 421 pierced by a passage 422 with a bend, having an inlet suitable for receiving the free end of the faucet 40 and having the opposite end of the bend 422 communicating with the inside of the chamber 18.

The chamber 18 is then closed at one of its ends (at the top in FIG. 7) by a leaktight cap 183 replacing the leaktight coupling 182 of FIG. 2, while the other end of the chamber 18 (at the bottom in FIG. 7) still has the leaktight coupling 181 that is used for discharging the water that has passed through the inside of the chamber 18.

Figure 8:
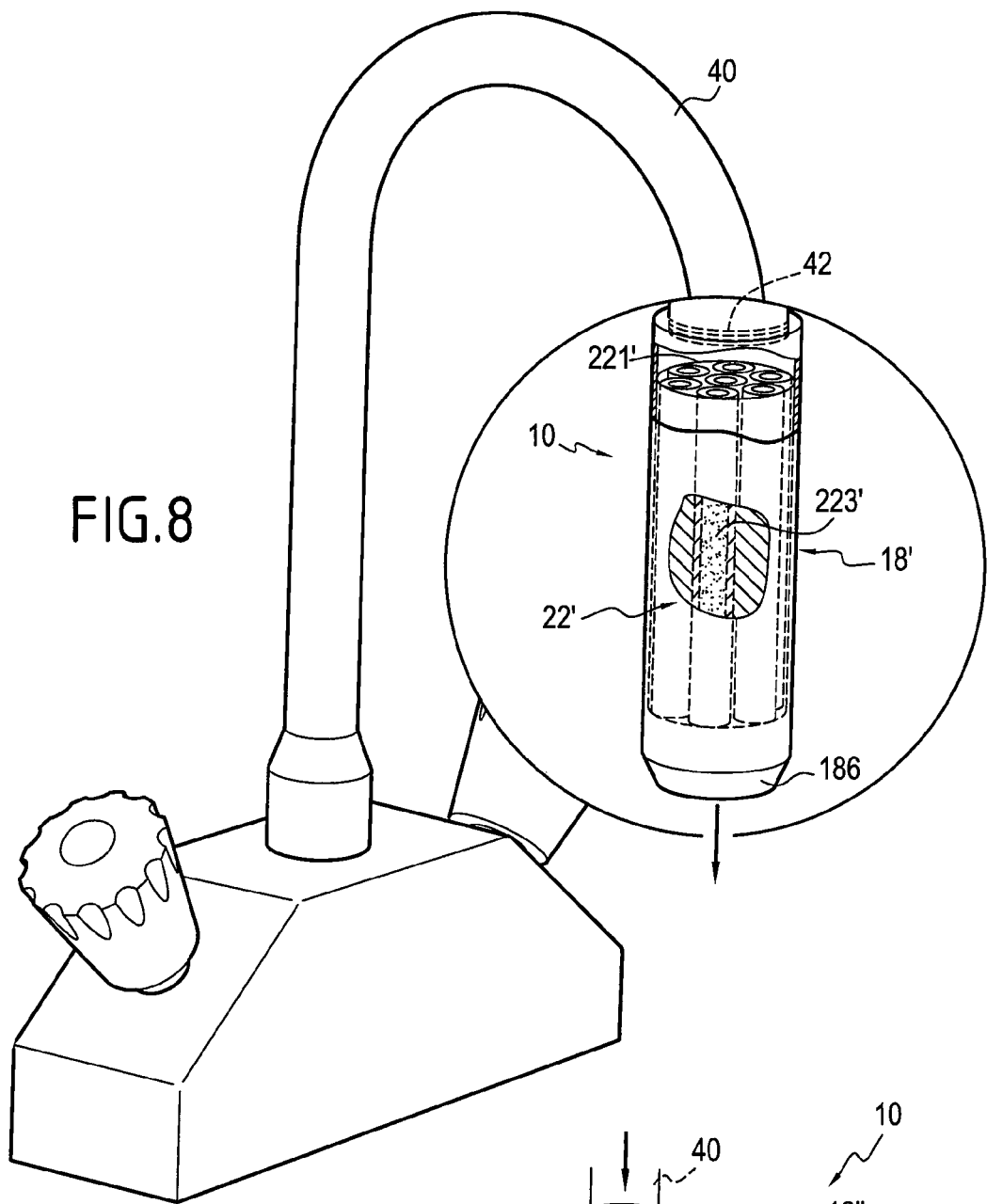
FIGS. 8 and 9 show two other solutions for making the variant in accordance with FIGS. 5 to 7.

FIG. 8 shows a first other embodiment of the variant shown in FIGS. 5 to 7 in which the device 10 is located directly at the end of a faucet 40. Under such circumstances, the quick-coupling system 42 is a threaded coupling mounted on the chamber 18' containing the capture means 22' and including a support 221' in the form of a housing tube provided with a plurality of through orifices, each capable of containing a capture element 223'. Each capture element 223' is in the form of a hollow glass tube having its inside wall coated in a layer of polydimethylsiloxane (PDMS) with a fraction of the flow of water passing through the chamber 18' at the outlet from the faucet 40 flowing thereover.

In FIG. 8, seven hollow glass tubes forming respective capture elements 223' are housed in seven support orifices 221'. Nevertheless, it should be understood that it is possible to provide a support 221' with a number of orifices that is larger or smaller than seven, or indeed that it suffices for at least one of the support orifices 221' to house a capture element 223' in order for the device 10 to function, i.e. to capture odor- and/or taste-generating substances present in the water flowing through the device 10. In FIG. 8, a tap-nozzle 186 is situated at the bottom portion of the chamber 18'.

In this first solution shown in FIG. 8, when it is desired to characterize the odor- and/or taste-generating substances that have been collected on the layer of polydimethylsiloxane (PDMS) coating the inside walls of the hollow glass tubes forming the capture elements 223', it suffices to remove the support 221' and remove at least one of the hollow glass tubes forming the capture elements 223' prior to performing the analysis.

Figure 9:
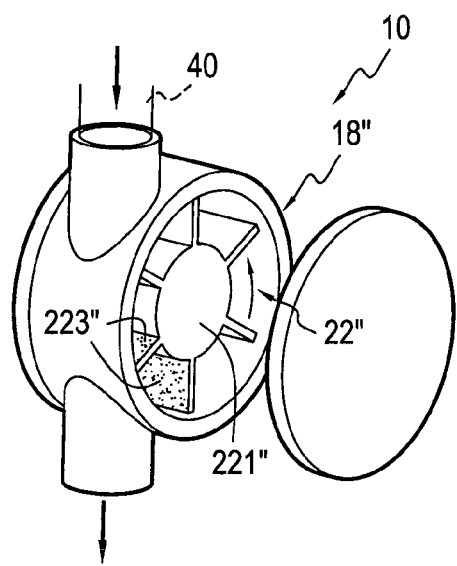

FIG. 9 shows a second other embodiment of the variant shown in FIGS. 5 to 7, in which the device 10 is directly connected to the end of a faucet 40. As can be seen in FIG. 9, the chamber 18" is connected to the endpiece of the faucet 40 via a suitable quick-coupling system 42 and it is in the form of a drum, the chamber 18 operating on the principle of a water mill by virtue of the capture means 22" that comprises:

a rotary shaft 221" suitable for turning relative to the chamber 18" in a direction orthogonal to the flow direction of water from the faucet 40, being offset from the flow axis of the water leaving the faucet 40; and blades 223" mounted on the rotary shaft 221" and covered in a layer of polydimethylsiloxane (PDMS) at least on the face over which the water passing through the chamber 18" flows at the outlet from the faucet 40.

It will be understood that the rotary shaft 221", serves as a support for the blades 223" which themselves form the moving capture elements 223" that act by sorption.

In this second solution shown in FIG. 9, when it is desired to characterize the odor- and/or taste-generating substances that have been collected by the layer of polydimethylsiloxane (PDMS) on the blades 223", it suffices to replace the chamber 18" with another chamber 18", or else it is possible to make provision for opening the chamber 18" and changing either one or more of the blades 223", or else the assembly formed by the support shaft 221" and the blades 223".

What is claimed is:

1. A device for capturing odor- and/or taste-generating substances present in water flowing in a water distribution network via a pipe comprising:

a chamber, through which water flows;

a support disposed in the chamber;

at least one capture element comprising a hollow glass tube including an inner surface, a layer consisting of polydimethylsiloxane on the inner surface, wherein an interior region bounded by the hollow glass tube and the layer is free of material, the at least one capture element being mounted on the support, wherein the at least one capture element is operable to capture the taste-generating substances or odor-generating substances present in the water by sorption on the layer of polydimethylsiloxane as the water flows over the inner surface layer of polydimethylsiloxane of the at least one capture element; and a hydraulic link and connection for coupling said chamber to said pipe.

2. The device according to claim 1 wherein materials forming the device do not give off compounds that could impede capture of odorous molecules.

3. The device according to claim 1 wherein said hydraulic link and connection comprises a quick-coupling system for coupling to an outlet faucet on user premises.

4. The device according to claim 1 wherein the support is in the form of a housing tube provided with a plurality of through orifices, each capable of containing a capture element.

* * * * *